United States Patent
van de Broek et al.

(10) Patent No.: US 7,462,336 B2
(45) Date of Patent: Dec. 9, 2008

(54) APPARATUS FOR PREPARING A DIALKYL CARBONATE

(75) Inventors: Jan van de Broek, Bergen op Zoom (NL); Stephan Bouwens, Bergen op Zoom (NL); Maarten Campman, Roosendaal (NL); Daniel Favre, Rensselaer, NY (US); Cornelis Adrianus Maria van Gool, Kapellen (BE); Leon Kalle, Almere (NL); George P. Moloney, Jr., Mechanicville, NY (US)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 575 days.

(21) Appl. No.: 11/167,649

(22) Filed: Jun. 27, 2005

(65) Prior Publication Data

US 2005/0265907 A1 Dec. 1, 2005

Related U.S. Application Data

(62) Division of application No. 10/250,067, filed on Jun. 2, 2003, now Pat. No. 6,977,308.

(60) Provisional application No. 60/401,916, filed on Aug. 8, 2002, provisional application No. 60/391,389, filed on Jun. 25, 2002.

(51) Int. Cl.
  C07C 69/96 (2006.01)
  B01J 8/04 (2006.01)
(52) U.S. Cl. ........................ 422/191; 558/277
(58) Field of Classification Search ........................ None
  See application file for complete search history.

(56) References Cited

U.S. PATENT DOCUMENTS

| | | | |
|---|---|---|---|
| 2,517,965 A | 8/1950 | Bohl | 260/463 |
| 3,153,008 A | 10/1964 | Fox | 260/47 |
| 4,182,726 A | 1/1980 | Illuminati et al. | 260/463 |
| 4,218,391 A | 8/1980 | Romano et al. | 260/463 |
| 4,318,862 A | 3/1982 | Romano et al. | 260/463 |
| 4,351,742 A | 9/1982 | Deuser et al. | 252/373 |
| 4,360,659 A | 11/1982 | Sikdar | 528/196 |
| 5,210,269 A | 5/1993 | Di Muzio et al. | 558/277 |
| 5,220,782 A | 6/1993 | Brown et al. | 60/39.02 |
| 5,527,943 A | 6/1996 | Rivetti et al. | 558/277 |
| 5,536,864 A | 7/1996 | Paret et al. | 558/277 |
| 5,599,965 A | 2/1997 | Kriesfalussy et al. | 558/277 |
| 5,685,957 A | 11/1997 | Rivetti et al. | 203/41 |
| 5,686,644 A | 11/1997 | Rivetti et al. | 558/277 |
| 5,780,663 A | 7/1998 | Mori et al. | 558/275 |
| 5,869,729 A | 2/1999 | Nishihira et al. | 558/277 |
| 2003/0055199 A1 | 3/2003 | Boden et al. | 528/196 |
| 2003/0060650 A1 | 3/2003 | Boden et al. | 558/227 |
| 2003/0092872 A1 | 5/2003 | Boden et al. | 528/196 |

FOREIGN PATENT DOCUMENTS

| | | |
|---|---|---|
| EP | 0 634 390 | 12/1994 |
| JP | 1994092905 | 4/1994 |
| WO | WO 03/016256 A1 | 2/2003 |

OTHER PUBLICATIONS

International Search Report Dated Oct. 23, 2003.
Building Permit for a new DMC Plant obtained byPolimeri Europa from the Ravenna, Italy local authority on May 22, 2001.
Translation of excerpts of Building Permit for a new DMC Plant obtained by Polimeri Europa frmo the Ravenna, Italy local authority on May 22, 2001.
M.M. Mauri, U. Romano, and F. Rivetti, Quad. Ing. Chim. Ital. (1985), vol. 21, No. 1-3, pp. 6-12.
U.S. Appl. No. 10/227,111, filed Aug. 23, 2002, Boden et al.
L. Cassar, Chim. Ind. (Milan) (1990), vol. 72, No. 1, pp. 18-22.
(anonymous) "GE licenses Enimont polycard know-how", European Chemical News, Nov. 13, 1989, pp. 44.
Shilling, et al. "Heat-Transfer Equipment" Section 11. PH Perry and C.H. Chilton, Eds., Perry's Chemical Engineer's Handbook. 7th Edition. pp. 11-1 through 11-118. (1999).
Fair, et al. "Gas Absorption and Gas Liquid System Design" Section 14. PH Perry and C.H. Chilton, Eds., Perry's Chemical Engineer's Handbook. 7th Edition. pp. 14-1 through 14-98. (1999).

*Primary Examiner*—Kamal A Saeed

(57) ABSTRACT

An apparatus for preparing a dialkyl carbonate comprises means for reacting an alkanol, oxygen, carbon monoxide, and a catalyst to form a mixture comprising a dialkyl carbonate, an alkyl chloroformate, hydrochloric acid, water, carbon dioxide, and carbon monoxide; means for separating from the mixture a gaseous fraction comprising carbon monoxide and alkyl chloroformate; and means for removing alkyl chloroformate from the gaseous fraction.

7 Claims, 3 Drawing Sheets

APPARATUS FOR PREPARING A DIALKYL CARBONATE

CROSS REFERENCE TO RELATED APPLICATIONS

This Application is a Divisional of U.S. application Ser. No. 10/250,067, filed Jun. 2, 2003, now U.S. Pat. No. 6,977,308 which in turn claims benefit of U.S. Application No. 60/391,389, filed Jun. 25, 2002 and U.S. application No. 60/401,916 filed on Aug. 8, 2002 the entire contents of which are incorporated herein by reference.

BACKGROUND OF INVENTION

Polycarbonate resins are useful materials valued for their physical and optical properties. Methods for the preparation of polycarbonate resins include interfacial processes and melt processes. In interfacial processes, as described, for example, in U.S. Pat. No. 4,360,659 to Sikdar, a bisphenol is reacted with phosgene in the presence of solvents. In melt processes, as described, for example, in U.S. Pat. No. 3,153,008 to Fox, a bisphenol is reacted with a diaryl carbonate. Melt processes are presently preferred because they avoid the use of phosgene and solvents.

Use of a melt process for polycarbonate synthesis requires an industrially efficient process for producing diaryl carbonates. There are several known processes for producing diaryl carbonates. One example of such a process is described by U.S. Pat. No. 4,182,726 to Illuminati et al. In this process, diaryl carbonates are produced by reacting dialkyl carbonates with aryl hydroxides (see Scheme I, below).

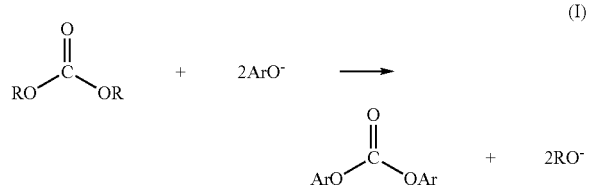

U.S. Pat. No. 4,182,726 also demonstrates that diaryl carbonates can be reacted with dihydric phenols to produce polycarbonates (see Scheme II, below).

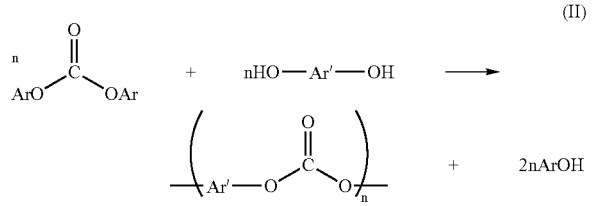

A preferred process for making dialkyl carbonates is illustrated in Scheme III, below, and described, for example, in U.S. Pat. No. 5,527,943 to Rivetti et al.; and U.S. Pat. Nos. 4,218,391 and 4,318,862 to Romano et al.

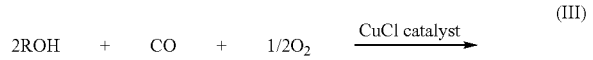

U.S. Pat. No. 5,527,943 (the '943 patent) also describes a known drawback of the dialkyl carbonate process according to Scheme (III): it produces water as a by-product. Also, hydrochloric acid (HCl) may be continuously added to the reaction mixture to maintain a desired molar ratio of chloride to copper. Therefore, HCl, CuCl catalyst, and water are typically found in the stream exiting the reactor vessel. Hydrochloric acid and copper chlorides are very corrosive in the presence of water, so equipment made from corrosion-resistant materials, such as glass-lined vessels, must be used in the reaction section of a chemical plant making dialkyl carbonates by this process. As corrosion-resistant equipment is expensive, there is a desire to minimize its use in the plant.

A plant for preparing dialkyl carbonates according to Scheme III may contain three sections: a reaction section for converting raw materials to dialkyl carbonate, a separation section for isolating the dialkyl carbonate from unreacted raw materials and by-products, and a purification section for removing water and further isolating the dialkyl carbonate. If the reaction is run with an excess of carbon monoxide, the separation section may contain a subsection, hereinafter referred to as the "cold wash unit", for removing organic impurities from the mixture of carbon monoxide and carbon dioxide exiting the reactor. The mixture of carbon monoxide and carbon dioxide may then be subjected to further separation and/or purification so that carbon monoxide can be recycled to the reactor.

The '943 patent teaches that one can minimize the amount of corrosion-resistant equipment required by removing the HCl from the process stream immediately after the reaction section. This eliminates the necessity of using expensive corrosion-resistant materials in the separation and purification sections of the plant. The '943 patent further suggests that removal of HCl and copper halide salts from the stream immediately after the reaction section can be accomplished by exposing the gas-liquid mixture produced by the reaction to a liquid stream consisting of one of the process fluids.

In view of the above, it was desirable to construct a plant wherein the HCl and any copper halide salts would be removed from the stream after the reaction section to avoid corrosion in downstream sections of the plant. However, a technique similar to that described by the '943 patent—removing HCl and copper salts by treatment of a vaporized feed in a column using a counterflowing azeotrope fluid from the reaction mixture—failed to prevent corrosion in the cold wash unit.

There is therefore a need for a dialkyl carbonate process that recognizes and eliminates the cause of corrosion in the cold wash unit.

SUMMARY OF INVENTION

The above-described and other drawbacks and disadvantages are alleviated by a method of preparing a dialkyl carbonate, comprising: reacting an alkanol, oxygen, carbon monoxide, and a catalyst to form a mixture comprising a dialkyl carbonate and an alkyl chloroformate; separating from the mixture a gaseous fraction comprising alkyl chloroformate; and removing alkyl chloroformate from the gaseous fraction.

BRIEF DESCRIPTION OF DRAWINGS

Referring now to the figures, wherein like elements are numbered alike.

DETAILED DESCRIPTION OF THE PREFERRED EMBODIMENTS

Figure 1:
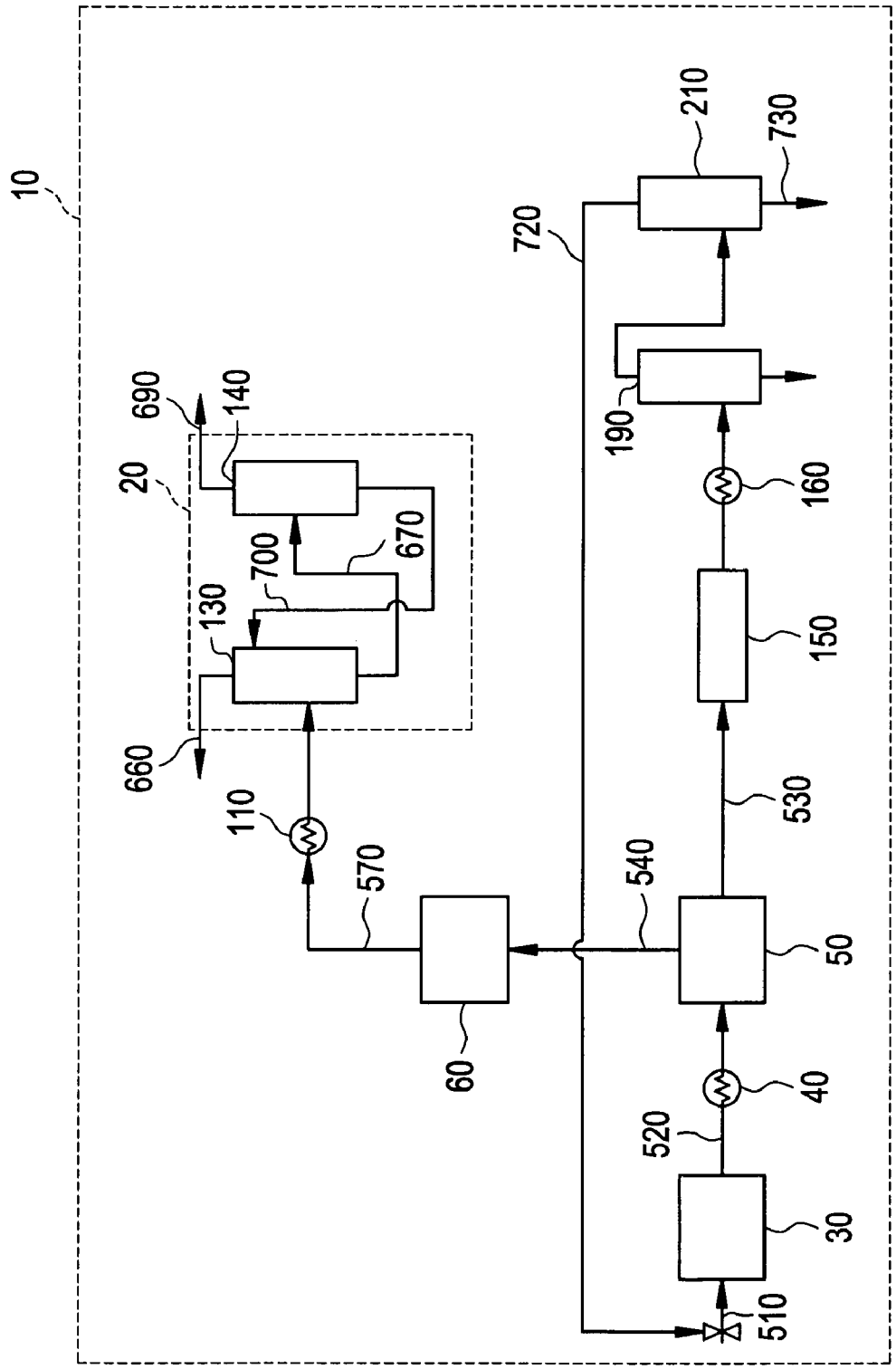
FIG. 1 is a simplified diagrammatic view of an apparatus that separates the reactor effluent into a gaseous fraction and a condensed fraction and removes alkyl chloroformate from the gaseous fraction, thereby preventing corrosion in the cold wash unit.

One embodiment of a method of preparing a dialkyl carbonate comprises: reacting an alkanol, oxygen, carbon monoxide, and a catalyst to form a mixture comprising a dialkyl carbonate and an alkyl chloroformate; separating from the mixture a gaseous fraction comprising alkyl chloroformate; and removing alkyl chloroformate from the gaseous fraction.

It has been discovered that dialkyl carbonate synthesis can form an alkyl chloroformate by-product that leads to problematic corrosion in the cold wash unit. For example, in the reaction of methanol, carbon monoxide, and oxygen to form dimethyl carbonate (hereinafter "DMC"), methyl chloroformate (hereinafter "MCF") may be formed as a by-product. The present inventors have found that when reactor effluent is separated from a liquid fraction and a gaseous fraction, the gaseous fraction may contain a portion of the alkyl chloroformate. This alkyl chloroformate in the gaseous fraction may react with alkanol and/or water to form significant amounts of corrosive HCl, which corrodes the cold wash unit. Therefore, it was determined that it is beneficial to remove alkyl chloroformate from the gaseous fraction before it enters the cold wash unit.

There is no particular limitation on the alkanol used in the method. Suitable alkanols include primary, secondary, and tertiary $C_1$-$C_{12}$ alkanols, with primary $C_1$-$C_6$ alkanols being preferred. Highly preferred alkanols include methanol.

Oxygen may be provided in any form, with gaseous forms being preferred. Suitable oxygen sources include, for example, air, and oxygen-containing gases having at least about 95 weight percent molecular oxygen, preferably at least about 99 weight percent molecular oxygen, based on the total weight of the oxygen-containing gas. Suitable oxygen-containing gases are commercially available from, for example, Air Products.

Carbon monoxide is preferably supplied as a carbon monoxide-containing gas having at least about 60 weight percent, preferably at least about 90 weight percent, more preferably at least about 95 weight percent, carbon monoxide, based on the total weight of the carbon monoxide-containing gas. Suitable carbon monoxide-containing gases are commercially available from, for example, Air Products.

Suitable catalysts may comprise metals such as iron, copper, nickel, cobalt, zinc, ruthenium, rhodium, palladium, silver, cadmium, rhenium, osmium, iridium, platinum, gold, mercury, and the like, and combinations comprising at least one of the foregoing metals. Preferred catalysts may comprise copper. A highly preferred catalyst comprises copper and chloride ion in a molar ratio of about 0.5 to about 1.5. Within this range, a molar ratio of at least about 0.8 may be preferred. Also within this range, a molar ratio of up to about 1.2 may be preferred. Highly preferred catalysts include cuprous chloride (CuCl) and cupric chloride ($CuCl_2$), with cuprous chloride being more highly preferred. During operation of the process, a suitable chloride ion concentration may be maintained by the addition of hydrochloric acid (HCl).

The catalyzed reaction of alkanol, oxygen, and carbon monoxide may be performed under conditions selected to maximize the yield of dialkyl carbonate while minimizing the degradation of dialkyl carbonate. Preferably, the reaction is performed at a temperature of about 50° C. to about 250° C. Within this range, the temperature may preferably be at least about 100° C. Also within this range, the temperature may preferably be up to about 150° C. The reactants preferably kept at a pressure of about 15 to about 35 bar gauge (barg). Within this range, a pressure of at least about 20 barg may be preferred. Also within this range, a pressure up to about 28 barg may be preferred. In the case of dual reactor systems, the catalyst may be recycled between tanks. The catalyst concentration should be sufficiently high to produce an acceptable yield, but it should be kept below a concentration that would cause precipitation of the catalyst in the reactor 30 or clogging of the equipment. The reactants alkanol, oxygen, and carbon monoxide are preferably added in a molar ratio of (about 0.5 to about 0.7):(about 0.04 to about 0.06):(about 0.8 to about 1.2), respectively. A highly preferred molar ratio of alkanol:oxygen:carbon monoxide is (about 0.6):(about 0.05):(about 1).

The amount of catalyst used relative to the reactants will depend on the identity of the catalyst. For example, when the catalyst comprises CuCl, a highly preferred catalyst concentration is about 40 to about 180 grams of CuCl per liter of reaction mixture. During operation, the catalyst may initially be added from a catalyst tank (not shown). Sufficient HCl is preferably added to the reactor from a hydrochloric acid tank (not shown) during the course of the reaction to maintain a molar ratio of Cu:Cl close to 1.0. The concentration of HCl is preferably continuously determined and controlled by the addition of HCl. A typical mass ratio for HCl feed to total liquid feed is about $1 \times 10^{-3}$ to about $3 \times 10^{-3}$.

FIG. 1 illustrates a dialkyl carbonate plant 10. The reaction of liquid reactants 510 (including alkanol and catalyst components) with oxygen and carbon monoxide in reactor 30 produces a mixture comprising a dialkyl carbonate and an alkyl chloroformate. The reaction mixture may further comprise water, carbon dioxide, and residual alkanol, oxygen, carbon monoxide, and catalyst components, as well as side-products such as alkyl chlorides and dialkyl ethers. The mixture is typically withdrawn from the reactor 30 in a gas/vapor form as reaction mixture 520. The term "vapor" is meant to refer to gaseous organic components of the mixture such as, for example, evaporated dialkyl carbonates, alcohols, alkyl chloroformates, etc., and to water vapor. That is, the term "vapor" refers to fluids having a boiling point of at least −50° C. at one atmosphere. In contrast, the term "gas" is meant to refer to the gaseous oxygen, carbon dioxide, carbon monoxide, and optional nitrogen. That is, the term "gas" refers to fluids having a boiling point less than −50° C. at one atmosphere. The vapor may be at least partially condensed in a first condenser 40, and fed to a first gas-liquid separator 50. The apparatus may optionally employ a single gas-liquid separator, or a plurality of (i.e., at least 2; preferably 2, 3, 4, 5, or more) gas-liquid separators. The first gas-liquid separator 50 may be kept at a pressure within about 10%, more preferably within about 1%, of the pressure of the reactor 30. The first gas-liquid separator 50 separates a first liquid fraction 530 and a first gaseous fraction 540. The first liquid fraction 530 proceeds via a liquid fraction alkyl chloroformate removal system 150 and a first heat exchanger 160 to an acid removal column 190 and an azeotrope column 210, ultimately producing an alkanol/dialkyl carbonate azeotrope 720 that is recycled to the reactor 30, and a water/dialkyl carbonate mixture 730 that proceeds to a purification section (not shown) for further purification.

The present inventors unexpectedly found that if the gaseous fraction 540 proceeded directly to a cold wash unit 20, the cold wash unit 20 suffered corrosion. Extensive studies revealed that the corrosion was due to a byproduct, alkyl chloroformate, formed in the reactor 30. As the reaction mixture 520 was separated in a gas-liquid separator, a portion of the alkyl chloroformate was present in the gaseous fraction, and its degradation in the cold wash fluid formed hydrochloric acid, leading to corrosion in the cold wash unit 20. After discovering this previously unrecognized problem, the present inventors devised various embodiments of a method and apparatus for removing alkyl chloroformate from the gaseous fraction to minimize corrosion in the subsections of the plant that handle the gaseous fraction.

One embodiment is depicted in FIG. 1. The first gaseous fraction 540, consisting mainly of carbon monoxide and carbon dioxide, enters the gaseous fraction alkyl chloroformate removal system 60, described in greater detail below, which produces an alkyl chloroformate-depleted first gaseous fraction 570. The alkyl chloroformate-depleted first gaseous fraction 570 proceeds via the chiller 110 to the cold wash unit 20. The cold wash unit 20 comprises a cold wash absorber 130, in which a cold wash fluid physically and selectively absorbs further organic contaminants from the alkyl chloroformate-depleted first gaseous fraction 570, and a cold wash regenerator 140, where the cold wash fluid is heated to evaporate the organic byproducts 690, which are sent to an incinerator (not shown).

The temperature of the cold wash fluid in the cold wash absorber 130 may be about −32° C. to about 0° C. Within this range, it may be preferred to use a temperature of at least about −20° C., more preferably at least about −15° C.

The temperature of the cold wash fluid in the cold wash regenerator 140 may be about 90° C. to about 125° C. Within this range, it may be preferred to use a temperature of at least about 100° C., more preferably at least about 103° C.

The purified carbon monoxide/carbon dioxide mixture 660, essentially free of organic contaminants, exits the cold wash absorber 130 and may, optionally, be treated to remove carbon dioxide or convert carbon dioxide to carbon monoxide before optional recycling to reactor 30. The cold wash fluid may be continuously recycled between the cold wash absorber 130 and the cold wash regenerator 140 via cold wash recycling from absorber to regenerator 670 and cold wash recycling from regenerator to absorber 700. The first liquid fraction 530 proceeds to the liquid fraction alkyl chloroformate removal system 150 and the first heat exchanger 160, which may at least partially vaporize the liquid fraction 530, to the acid removal column 190, which removes hydrochloric acid and metallic impurities from the liquid fraction, to the azeotrope column 210. The azeotrope column 210 produces an alkanol/dialkyl carbonate azeotrope 720 that may be recycled to reactor 30 (via combination with liquid reactants 510) and a water/dialkyl carbonate mixture 730 that proceeds to a purification section (not shown). Various methods and apparatus associated with the liquid fraction alkyl chloroformate removal system 150 are described in co-pending U.S. application Ser. Nos. 09/682,284, 09/682,285, and 09/682,286, all filed 14 Aug. 2001.

The gaseous fraction alkyl chloroformate removal system 60 and the liquid fraction alkyl chloroformate removal system 150 may utilize any technique suitable for removing alkyl chloroformate from the gaseous and liquid fractions, respectively. It will be understood that the terms "remove", "removing", and "removal" in reference to a particular chemical species in a mixture encompass any chemical or physical process that reduces the concentration of the species in the mixture. The alkyl chloroformate may be removed from the gaseous fraction and the liquid fraction by any method. Some preferred methods for removing the alkyl chloroformate by chemical reaction include heating, increasing pressure, increasing residence time, adding a polar solvent, exposing to a stoichiometric reagent, exposing to a catalytic reagent such as an ion exchange resin, and the like, and combinations comprising at least one of the foregoing techniques. Some preferred methods for removing the alkyl chloroformate by separation include cooling, decreasing pressure, adsorbing, absorbing, condensing, separating with a membrane (including gas and liquid membrane separation), pervaporating, and the like, and combinations comprising at least one of the foregoing techniques.

In one embodiment, the alkyl chloroformate is removed by reaction with water (see Scheme IV) or alkanol (see Scheme V).

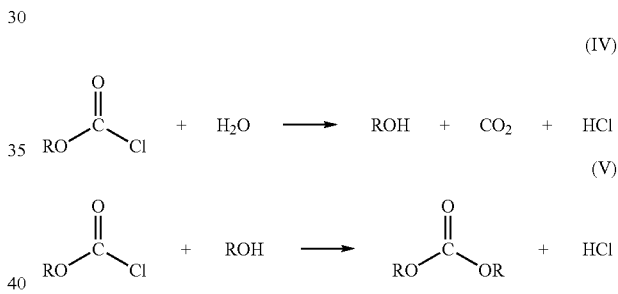

Figure 2:
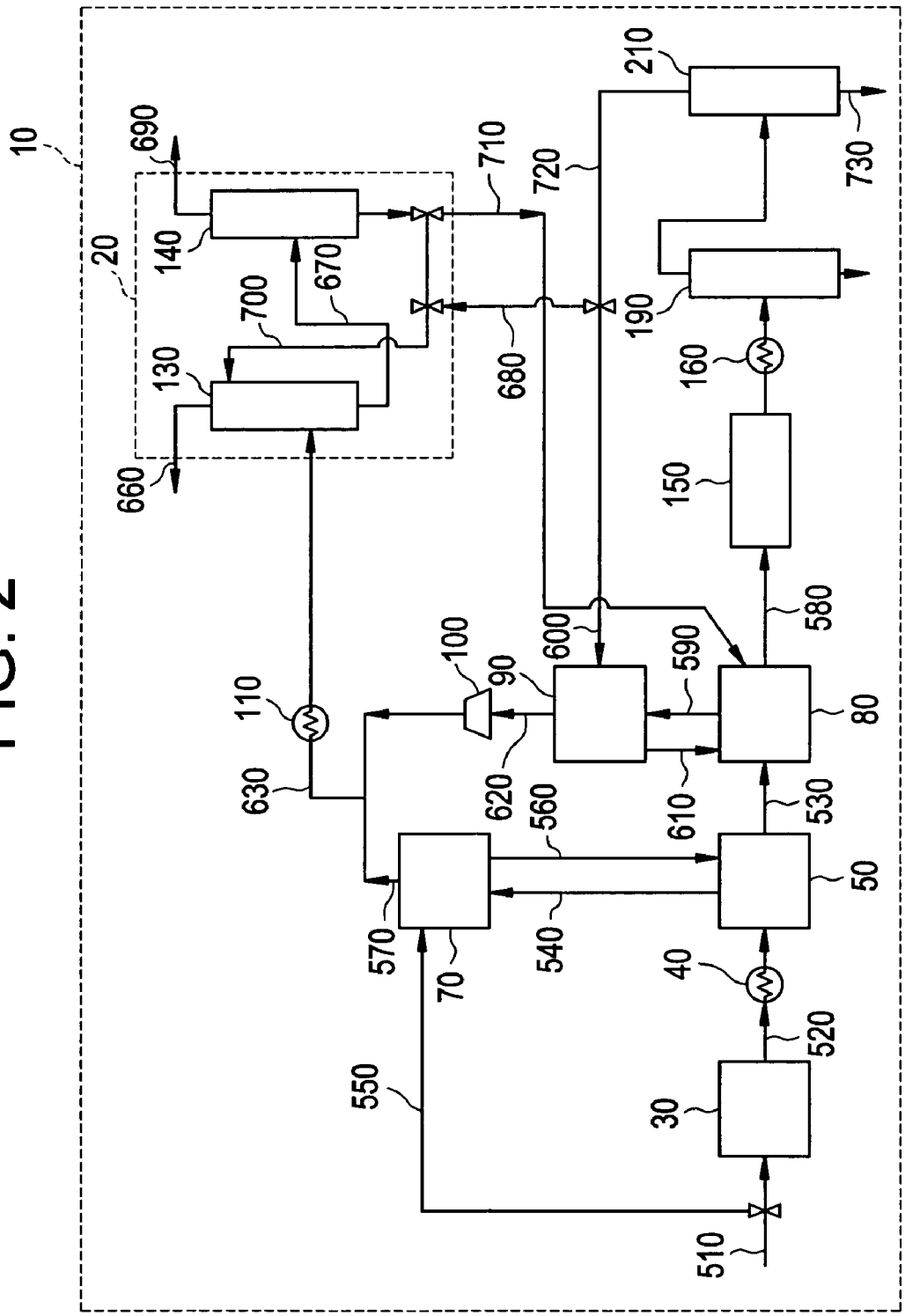
FIG. 2 is a simplified diagrammatic view of an apparatus comprising two gas-liquid separators, each of which feeds a gaseous fraction to an absorber that removes alkyl chloroformate. The gas streams for the two absorbers are recombined and sent to the cold wash unit.

A preferred embodiment of the method and apparatus is depicted in the simplified diagram of FIG. 2. In dialkyl carbonate plant 10, liquid reactants 510 (e.g., alkanol) enter reactor 30, where reaction mixture 520 is produced. The reaction mixture 520 proceeds via a first condenser 40 to a first gas-liquid separator 50, which produces a first liquid fraction 530 and a first gaseous fraction 540. The first liquid fraction 530 proceeds to a second gas-liquid separator 80, which produces a second liquid fraction 580 and a second gaseous fraction 590. The apparatus may employ a single gas-liquid separator, or a plurality of (e.g., 2, 3, 4, 5, or more) gas-liquid separators. The first gas-liquid separator 50 may be kept at a pressure within about 10%, more preferably within about 1%, of the pressure of the reactor 30. The second gas-liquid separator 80 may preferably have a pressure less than about 20% of the pressure of the reactor 30 (e.g., preferably less than 3 bar gauge, more preferably about 0.2 bar gauge) to preferably achieve separation of at least about 90%, more preferably at least 95%, by weight of the remaining gas in the mixture. It is preferred that the vapor in the mixture be in a partially condensed form (i.e., at least about 10% condensed), more preferably a fully condensed form (i.e., at least about 90% condensed), before entering the first gas-liquid separator 50, and between the first gas-liquid separator 50 and the second gas-liquid separator 80. The first gaseous fraction 540 and the second gaseous fraction 590 proceed, respectively, to the first absorber 70 and the second absorber 90. In the first absorber 70, alkyl chloroformate is removed from the first gaseous fraction 540 by absorption in a first fresh absorbing fluid 550, which represents a portion of the liquid reactants 510, which in turn preferably comprise the alkanol used in dialkyl carbonate synthesis. In the second absorber 90, alkyl chloroformate is removed from the second gaseous fraction 590 by absorption in a second fresh absorbing fluid 600, which represents a portion of the alkanol/dialkyl carbonate azeotrope 720 produced by the azeotrope column 210. The first fresh absorbing fluid 550 and the second fresh absorbing fluid 600 may preferably comprise less than about 100 parts per million by weight, more preferably less than about 10 parts per million by weight, yet more preferably less than about 1 part per million by weight, of chloride ion, which is a product of the degradation of alkyl chloroformate prior to entering the respective absorbers. The first and second fresh absorbing fluids 550 and 600 preferably have a temperature of about −10° C. to about 40° C. Within this range, it may be preferred to use an absorbing fluid temperature of up to about 30° C., more preferably up to about 25° C. In general, the absorbing fluid temperature will be below the atmospheric boiling point of the alkyl chloroformate, but above the atmospheric boiling point of the alkyl chloride or the dialkyl ether derived from the alkanol reactant. In this way, the alkyl chloride and the dialkyl ether may be separated from the gaseous fraction in the cold wash unit.

The first used absorbing fluid 560 and the second used absorbing fluid 610, which comprise absorbed alkyl chloroformate, are each preferably directed to a point upstream of liquid fraction alkyl chloroformate removal system 150, so that the alkyl chloroformate absorbed from the gaseous fractions is chemically destroyed in a corrosion-resistant section of the plant. For example, as depicted in FIG. 2, the first used absorbing fluid 560 from first absorber 70 may be directed to the first gas-liquid separator 50, and the second used absorbing fluid 610 from second absorber 90 may be directed to the second gas-liquid separator 80. The first used absorbing fluid 560 from first absorber 70 may be directed to reactor 30.

Exiting the second absorber 90, the alkyl chloroformate-depleted second gaseous fraction 620 is compressed via compressor 100 to a pressure within about 2 barg of that of the alkyl chloroformate-depleted first gaseous fraction 570 exiting the first absorber 70. The combined alkyl chloroformate-depleted gaseous fractions 630 proceed via a chiller 110 to the cold wash unit 20, which is similar to that described above for FIG. 1 with two exceptions. First, the cold wash fluid comprises alkanol/dialkyl carbonate azeotrope 680, which is a portion of the alkanol/dialkyl carbonate azeotrope 720 exiting the azeotrope column 210. Second, a portion of the cold wash fluid, designated cold wash fluid to second gas-liquid separator 710, is directed from the cold wash regenerator 140 to the second gas-liquid separator 80.

In the embodiment illustrated in FIG. 2, the first absorber 70 and the second absorber 90 collectively constitute the gaseous fraction alkyl chloroformate removal system 60.

In general, there is no particular limitation on the composition of the absorbing fluid using in the first absorber 70 and the second absorber 90, except that it absorbs the alkyl chloroformate. For simplicity and efficiency, it may be preferred to employ an existing process fluid from the plant as the absorbing fluid. For example, the absorbing fluid may comprise the alkanol that is used as the starting material for alkyl chloroformate synthesis. The absorbing fluid may also comprise the dialkyl carbonate product, alone or in combination with the alkanol. Suitable absorbing methods and equipment are known in the art and described, for example in R. H. Perry and C. H. Chilton, Eds., "Perry's Chemical Engineer's Handbook, 7$^{th}$ Edition", McGraw-Hill, 1999, Chapter 14: Gas Absorption and Gas-Liquid System Design. Commercial suppliers of absorbing equipment include, for example, Nutter Engineering, Kock-Glitsch, Jaeger Products, Rashig AG, and Vereinigte-Füllkörper-Fabriken (VFF).

Figure 3:
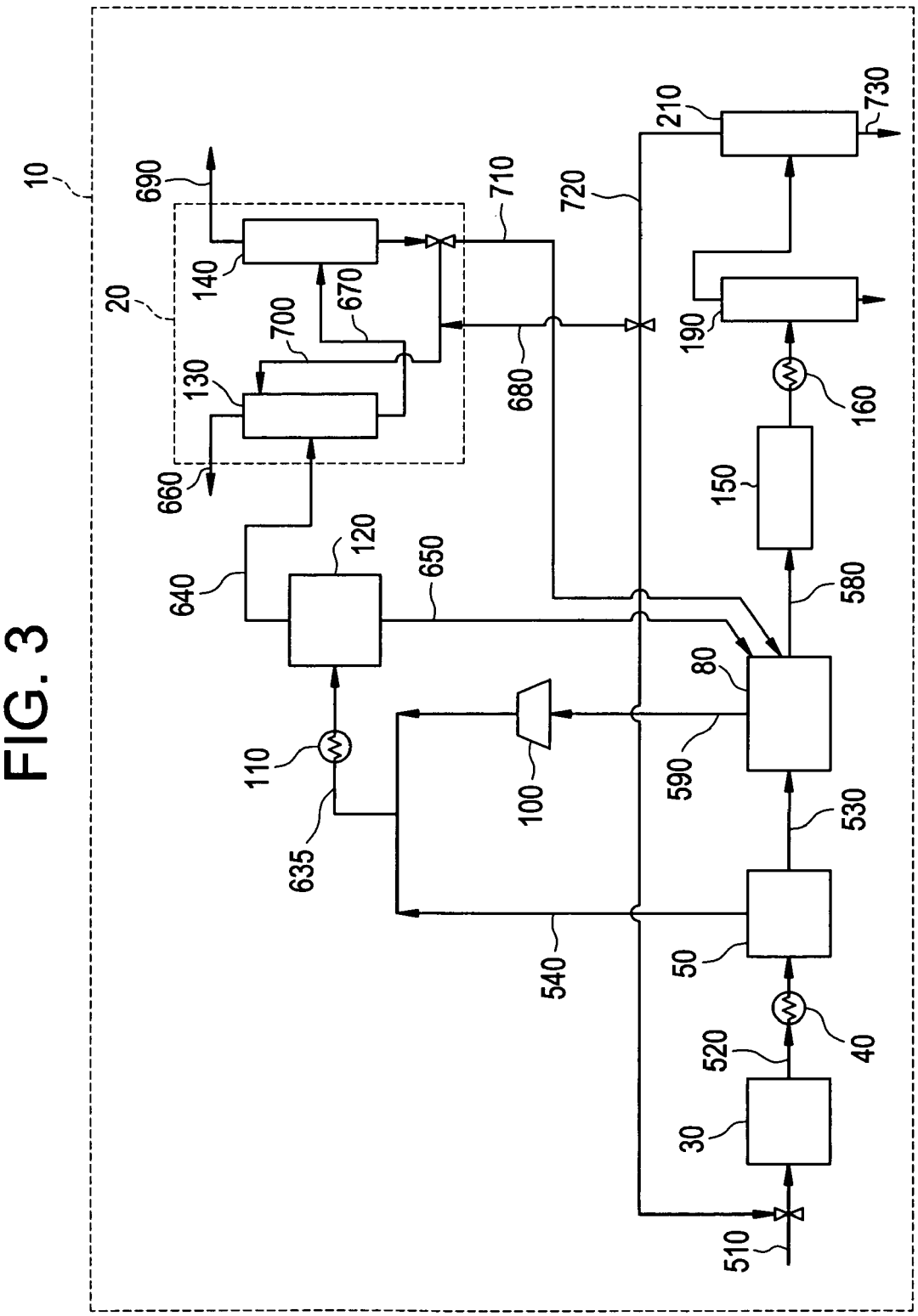
FIG. 3 is a simplified diagrammatic view of an apparatus in which the gaseous fractions from two gas-liquid separators are combined and sent to a knock out drum before entering the cold wash unit.

In another preferred embodiment, the alkyl chloroformate may be removed from the gaseous fraction by partial condensation. For example, as illustrated in FIG. 3, the combined gaseous fractions 635 from the gas-liquid separators may be passed via a chiller 110 to a knock out drum 120 to separate the condensed alkyl chloroformate while leaving the third gaseous fraction 640, which contains carbon monoxide and carbon dioxide, in the gas phase. A plurality of knock out drums 120 (e.g., 2, 3, 4, 5, or more knock out drums) may be employed. The temperature of the knock out drum 120 is preferably about −50° C. to about 0° C. Within this range, it may be preferred to use a temperature of at least about −40° C., more preferably at least about −30° C. Also within this range, it may be preferred to use a temperature of up to about −10° C., more preferably up to about −20° C. Suitable condensing equipment is known in the art and described, for example, R. H. Perry and C. H. Chilton, Eds., "Perry's Chemical Engineer's Handbook, 7$^{th}$ Edition", McGraw-Hill, 1999, Chapter 11: Heat Transfer Equipment, and commercially available as, for example, shell and tube heat exchangers and plate heat exchanges from Alfa Laval Thermal AB, API Schmidt-Bretten and Kurose Chemical Equipment Co. Ltd. As shown in FIG. 3, the third liquid fraction 650 produced in the knock out drum 120 may be sent to the second gas-liquid separator 80. Alternatively, the third liquid fraction 650 may be sent to the first gas-liquid separator 50 or combined with the liquid reactants 510. In any of these cases, alkyl chloroformate present in the third liquid fraction 650 may be removed in liquid fraction alkyl chloroformate removal system 150. Second liquid fraction 580 proceeds downstream as described for FIG. 2. Alkyl chloroformate removed from the gaseous fractions is sent to the liquid fraction alkyl chloroformate removal system 150, which removes alkyl chloroformate from the liquid fraction. For example, the liquid fraction alkyl chloroformate removal system 150 may hold the second liquid fraction 580 at a temperature of about 50° C. to about 80° C. and for a residence time of about 1 hour to about 10 hours.

In the embodiment illustrated in FIG. 3, the knock out drum 120 constitutes the gaseous fraction alkyl chloroformate removal system 60.

It may be preferred to remove at least about 50 percent, more preferably at least about 90 percent, yet more preferably at least about 95 percent, even more preferably at least about 99 percent, of the alkyl chloroformate from the gaseous fraction. In one embodiment, it may be preferred to reduce the alkyl chloroformate concentration in the gaseous fraction to less than about 50 ppm, more preferably less than about 10 ppm, yet more preferably less than about 1 ppm.

When the alkyl chloroformate is physically removed from the gaseous fraction and subsequently combined with a liquid fraction, it is preferably removed from the liquid fraction by a method that minimizes loss of the desired dialkyl carbonate product. Specifically, it may be preferred to remove less than about 10%, more preferably less than about 5%, yet more preferably less than about 1%, of the dialkyl carbonate. Although the method may be described as "removing less than about 10% of said dialkyl carbonate", it will be understood that the concentration of dialkyl carbonate need not be reduced and may even increase. For example, the concentration of dialkyl carbonate may increase if the Scheme V reaction of alkyl chloroformate with alkanol forms dialkyl carbonate faster than dialkyl carbonate decomposes due to other reactions.

In a preferred embodiment, the cold wash unit 20 and portions of the plant downstream from the azeotrope column 210 are not corrosion-resistant. The reactor 30, the first gas-liquid separator 50, the second gas-liquid separator 80, the first absorber 70, and the second absorber 90 are preferably corrosion-resistant. For example, these components may be glass lined. The term "corrosion-resistant" is meant to describe a material capable of withstanding an HCl content of 2000 ppm at a temperature of about 50° C. to about 135° C. in the reaction mixture without substantial corrosion in a relatively brief time period (e.g., six months). Glass lined vessels, precious metal (e.g., tantalum) lined vessels would be considered corrosion-resistant. The term "medium corrosion-resistant" is meant to describe a material capable of withstanding an HCl content of 2000 ppm at a temperature of about 0° C. to about 55° C. without substantial corrosion in a relatively brief period (e.g., six months). Special steels such as HASTELLOY® and CHROMALLOY® would be considered medium corrosion-resistant materials. The azeotrope column 210 may be made, at least in part, from medium corrosion-resistant materials. In a preferred embodiment, the bottom of the azeotrope column 210 may be made from a medium corrosion-resistant steel, whereas the top of the column can be made from ordinary stainless steel.

The invention is further illustrated by the following non-limiting examples.

EXAMPLE 1

In a dimethyl carbonate plant lacking a means of removing methyl chloroformate from the gaseous fraction, severe corrosion was observed in circulation pumps, heat exchangers, piping, and various components of a cold wash unit. The corrosion was so severe that these parts, many of which were fabricated from carbon steel, needed to be replaced early in their expected lifetimes.

Referring to FIG. 2, but with the understanding that the plant lacked any gaseous fraction alkyl chloroformate removal system, methyl chloroformate was detected in first liquid fraction 530, in cold wash recycling from regenerator to absorber 700, in second gaseous fraction 590 (1320 ppm), and in first gaseous fraction 540 (86 ppm). The chloride concentration in cold wash recycling fluid was determined to have a mean concentration of 748 ppm with a standard deviation of 365 ppm.

Methyl chloroformate was detected by quenching with diisobutyl amine to convert the methyl chloroformate to N,N'-diisobutyl methyl carbamate. The amount of N,N'-diisobutyl methyl carbamate was then analyzed via titration with a standard silver nitrate solution to quantify the amount of ionic chloride present. The amount of methyl chloroformate could then be inferred by analyzing the original sample for ionic chloride. The difference in chloride concentration was equal to the methyl chloroformate concentration because each equivalent of methyl chloroformate liberates one equivalent of ionic chloride upon derivatization. Alternatively, gas chromatography was sometimes used for direct analysis of the N,N'-diisobutyl methyl carbamate using an internal standard.

EXAMPLE 2

The plant was modified to a configuration similar to that depicted in FIG. 3 by installation of a chiller 110 and knock out drum 120. The chiller 110 cooled the combined gaseous fractions 635 to about 5° C. The combined gaseous fractions 635 were then further cooled to about −20° C. to about −30° C. and sent through a knock-out drum before entering the absorption column of the coldwash system. After implementation, the chloride concentration in cold wash recycling from regenerator to absorber 700 was reduced to a mean of 50.7 ppm with a standard deviation of 17.4 ppm, corresponding to a 93% reduction in chloride concentration compared to the plant lacking any means of removing methyl chloroformate from the gaseous fraction.

EXAMPLE 3

The plant was modified by installation of a first absorber 70 and second absorber 90 in a configuration similar to that shown in FIG. 2. For both absorbers, the absorption liquid was an azeotropic mixture of dimethyl carbonate and methanol. The liquid discharge of the first absorber 70 was sent by pumping to reactor 30, and the liquid discharge of the second absorber 90 was sent to the second gas-liquid separator 80. After implementation, the chloride concentration in cold wash recycling from regenerator to absorber 700 was reduced to a mean of 0.25 ppm with a standard deviation of 0.57 ppm, confirming the near elimination of methyl chloroformate and chlorides in the gas streams treated by the cold wash unit 20.

The examples above show that removing alkyl chloroformate from the gaseous fraction is an effective means of preventing corrosion caused by chloride ion in the cold wash unit.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. An apparatus for preparing a dialkyl carbonate, comprising:
   means for reacting an alkanol, oxygen, carbon monoxide, and a catalyst to form a mixture comprising a dialkyl carbonate, an alkyl chloroformate, hydrochloric acid, water, carbon dioxide, and carbon monoxide;
   means for separating from the mixture a gaseous fraction comprising carbon monoxide and alkyl chloroformate; and
   means for removing alkyl chloroformate from the gaseous fraction.

2. An apparatus for preparing a dialkyl carbonate, comprising:
   a reactor for producing a mixture comprising a dialkyl carbonate, carbon monoxide, and an alkyl chloroformate;
   a gas-liquid separator for separating from the mixture a gaseous fraction comprising carbon monoxide and alkyl chloroformate, wherein the gas-liquid separator is in fluid communication with the reactor; and
   a knock out drum for removing alkyl chloroformate from the gaseous fraction, wherein the knock out drum is in fluid communication with the gas-liquid separator.

3. An apparatus for preparing a dialkyl carbonate, comprising:
- a reactor for producing a mixture comprising a dialkyl carbonate, carbon monoxide, and an alkyl chloroformate;
- a gas-liquid separator for separating from the mixture a gaseous fraction comprising carbon monoxide and alkyl chloroformate, wherein the gas-liquid separator is in fluid communication with the reactor; and
- an absorber for removing alkyl chloroformate from the gaseous fraction, wherein the absorber is in fluid communication with the gas-liquid separator.

4. The apparatus of claim 3, further comprising a cold wash unit for removing organic impurities from the gaseous fraction, wherein the cold wash unit is in fluid communication with the reactor and the absorber.

5. An apparatus for preparing a dialkyl carbonate, comprising:
- a reactor for reacting an alkanol, oxygen, carbon monoxide, and a catalyst to a produce a reaction mixture comprising a dialkyl carbonate, an alkyl chloroformate, hydrochloric acid, water, and carbon dioxide;
- a first gas-liquid separator for separating from the reaction mixture a first liquid fraction and a first gaseous fraction comprising carbon monoxide and alkyl chloroformate, wherein the first gas-liquid separator is in fluid communication with the reactor; and
- a second gas-liquid separator for separating from the first liquid fraction a second liquid fraction and a second gaseous fraction comprising carbon monoxide and alkyl chloroformate, wherein the second gas-liquid separator is in fluid communication with the first gas-liquid separator;
- a first absorber for removing the alkyl chloroformate from the first gaseous fraction, wherein the first absorber is in fluid communication with the first gas-liquid separator; and
- a second absorber for removing the alkyl chloroformate from the second gaseous fraction, wherein the second absorber is in fluid communication with the second gas-liquid separator.

6. The apparatus of claim 5, further comprising a cold wash unit for removing organic impurities from the first gaseous fraction and the second gaseous fraction, wherein the cold wash unit is in fluid communication with the first absorber and the second absorber.

7. The apparatus of claim 5, further comprising a compressor in fluid communication with the second absorber.

* * * * *